(12) United States Patent
Dirks et al.

(10) Patent No.: US 9,903,673 B1
(45) Date of Patent: Feb. 27, 2018

(54) INTELLIGENT BALL FOR MONITORING AND DIAGNOSIS OF HEAT EXCHANGER TUBE HEALTH

(71) Applicant: Sentinel Diagnostics, LLC, North Liberty, IA (US)

(72) Inventors: Charles B. Dirks, North Liberty, IA (US); Brian G. Jamieson, Severna Park, MD (US); Michael A. Crocker, Iowa City, IA (US)

(73) Assignee: Sentinel Diagnostics, LLC, North Liberty, IA (US)

( * ) Notice: Subject to any disclaimer, the term of this patent is extended or adjusted under 35 U.S.C. 154(b) by 48 days.

(21) Appl. No.: 15/259,491

(22) Filed: Sep. 8, 2016

Related U.S. Application Data

(60) Provisional application No. 62/233,384, filed on Sep. 27, 2015.

(51) Int. Cl.
*A61B 5/04* (2006.01)
*F28F 27/00* (2006.01)
*F28D 1/053* (2006.01)
*F28F 19/00* (2006.01)
*F28G 13/00* (2006.01)
*A61L 2/10* (2006.01)
(Continued)

(52) U.S. Cl.
CPC .............. *F28F 27/00* (2013.01); *A61L 2/10* (2013.01); *F28D 1/05316* (2013.01); *F28F 19/00* (2013.01); *F28G 13/00* (2013.01); *G01K 1/14* (2013.01); *G01N 27/9033* (2013.01); *G01N 29/04* (2013.01); *G01N 29/2437* (2013.01); *F28F 2265/16* (2013.01); *G01N 2291/0289* (2013.01)

(58) Field of Classification Search
CPC ........ F28F 27/00; F28F 19/00; F28F 2265/16; A61L 2/10; F28D 1/05316; F28G 13/00; G01K 1/14; G01N 27/9033; G01N 29/04; G01N 29/2437; G01N 2291/0289; G01N 29/221; G01N 29/223; G01N 2291/044; G01N 2291/2636; G01N 29/265; G01B 17/00; G01B 17/02; G01B 17/025; F24F 11/0086; F24F 2011/0091; Y10S 165/001; Y10T 137/2836
USPC .................................. 73/622, 623; 165/11.1
See application file for complete search history.

(56) References Cited

U.S. PATENT DOCUMENTS 2,799,157 A * 7/1957 Pohlman .............. G01N 29/265
                                                          310/336
4,920,804 A * 5/1990 Iwamoto .............. G01N 29/265
                                                          73/623
(Continued)

*Primary Examiner* — Justin Jonaitis
(74) *Attorney, Agent, or Firm* — Shuttleworth & Ingersoll, PLC; Jason Sytsma

(57) ABSTRACT

An intelligent ball sensor assembly for use with a heat exchanger system, includes a mechanically compliant ball having a recess formed therein. At least one sensor positioned on the ball is configured to gather selected information regarding a heat exchanger system. Signal conditioning control/transmission circuitry is operatively connected to the at least one sensor. A power source is operatively connected to the at least one sensor and the signal conditioning control/transmission circuitry. The sensor and the signal conditioning control/transmission circuitry cooperate to gather information about the status, health and efficiency of the heat exchanger system.

22 Claims, 1 Drawing Sheet

(51) Int. Cl.
*G01N 29/24* (2006.01)
*G01K 1/14* (2006.01)
*G01N 27/90* (2006.01)
*G01N 29/04* (2006.01)

(56) References Cited

U.S. PATENT DOCUMENTS

| | | | | |
|---|---|---|---|---|
| 5,062,300 | A * | 11/1991 | Vallee | G01N 29/221 |
| | | | | 73/623 |
| 5,090,259 | A * | 2/1992 | Shishido | G01N 21/954 |
| | | | | 324/220 |
| 5,313,838 | A * | 5/1994 | Gondard | G01N 29/265 |
| | | | | 324/220 |
| 5,471,879 | A * | 12/1995 | Vinot | G01N 29/221 |
| | | | | 73/622 |
| 9,791,222 | B2 * | 10/2017 | Jiang | F28G 1/12 |
| 2011/0162454 | A1 * | 7/2011 | Paulson | G01N 29/043 |
| | | | | 73/592 |

* cited by examiner

INTELLIGENT BALL FOR MONITORING AND DIAGNOSIS OF HEAT EXCHANGER TUBE HEALTH

This Application claims priority to Provisional Application No. 62/233,384 filed on Sep. 27, 2015, the contents of which are hereby incorporated by reference herein.

BACKGROUND

This disclosure relates generally to the monitoring and diagnosing of heat exchanger system health and more particularly to the use of intelligent balls for enabling this monitoring and diagnosing.

The most commonly practiced method for assessing the state of a heat exchanger, and in particular the individual tubes that come in contact with the working fluid, is to open the unit and examine each individual tube manually. This is a highly labor-intensive process and leads to substantial down time and associated costs as the unit is taken apart and examined.

Specific measurements used during tube inspection include eddy current sensors and ultrasonic probes, as well as simple video inspection with a fiberscope or video camera. These instruments, which are inserted manually into the tubes one at a time, give an indication of wall thinning and cracking.

U.S. Pat. No. 8,863,820, issued to Laursen et al. entitled, "MEASUREMENT DEVICE FOR HEAT EXCHANGER AND PROCESS FOR MEASURING PERFORMANCE OF A HEAT EXCHANGER," discloses a temperature measurement device in combination with a furnace heat exchanger. An instrumented heat tracer sensor is launched into the heat exchanger which records the temperature of the fluid and performance at data points along the length of the heat exchanger. If a spike in the temperature is measured and recorded, since the speed of the heat tracer sensor is known, the location of the temperature increase is known which infers a burn through in the furnace. A three way valve includes a retrieve port, a chamber port, and a launch port. A small sensor control pump and a large heat exchanger flow pump propel the heat tracer sensor through the system. A plastic chamber retains the heat tracer sensor for interrogation and downloading information when the sensor is not in use in the heat exchanger. A control station communicates with the heat tracer sensor and extracts the stored temperature data therefrom. The Laursen patent does not describe assessing comprehensive heat exchanger health, assessing flow rates inside of exchanger tubes, or determining in which tube temperature measurements are taken.

SUMMARY

In one aspect, the disclosure provides an intelligent ball sensor assembly for use with a heat exchanger system including; a) a mechanically compliant ball having a recess formed therein; b) at least one sensor positioned on the ball configured to gather selected information regarding a heat exchanger system; c) signal conditioning control/transmission circuitry operatively connected to the at least one sensor; and, d) a power source operatively connected to said at least one sensor and said signal conditioning control/transmission circuitry. The at least one sensor and the signal conditioning control/transmission circuitry cooperate to gather information about the status, health and efficiency of the heat exchanger system.

In one embodiment, the at least one sensor comprises a piezoelectric sensor configured to measure reflected ultrasound intensity, which is transmitted to a base station and analyzed upon arrival at a ball trap, in order to determine the state of health and mechanical integrity of a exchanger tube of the heat exchanger system and diagnose cracks, scaling, pinholes, wall thinning, etc.

In another broad aspect, the disclosure describes a heat exchanger system that includes a heat exchanger assembly including a plurality of plenums; a plurality of heat exchange tubes operatively connected to said plenums; and, a ball trap operatively connected to the plurality of plenums. A number of intelligent ball sensor assemblies, as discussed above, are configured to operate within the heat exchanger assembly.

Thus, the disclosure provides a method for monitoring heat exchanger tube health without requiring the system to be shut down and disassembled and without operator intervention. The method is affordable and robust, and can provide a continuous stream of data that allows continuous frequent inspections. The intelligent ball technology of this disclosure can also be used to optimize heat exchanger parameters such as flow (e.g. by determining the ideal state of pumps and valves) which, in turn, enables intelligent decisions to improve energy efficiency. This technology can allow the scheduling of routine maintenance such as tube cleaning, or can be used in conjunction with cleaning by objects inserted or released into the heat exchanger during normal operation (e.g. compliant balls). The cleaning balls used in current systems are "dumb" and serve to keep the condenser tubes clean. Subsequently, the "intelligent balls" of the present disclosure and the regular (dumb) sponge rubber balls can be operated together to provide both preventative cleaning and active data capture from the heat exchanger.

Unlike the prior art, in some embodiments, the present system can assess comprehensive heat exchanger health including such parameters as wall pitting, cracking and thinning, scaling, mechanical problems with ancillary systems such as pumps, biofouling or leakage of coolant. In some embodiments, it can assess flow rates inside the exchanger tubes. Furthermore, in some embodiments, it can precisely determine the tube in which a temperature measurement is taken.

Other objects, advantages, and novel features will become apparent from the following detailed description when considered in conjunction with the accompanying drawings.

DETAILED DESCRIPTION

Figure 1:
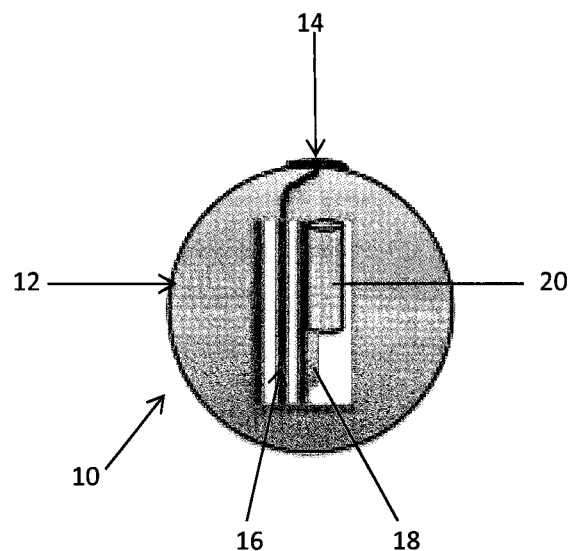
FIG. 1 is a schematic illustration of an intelligent ball sensor assembly of the present disclosure.

Referring now to the drawings and the characters of reference marked thereon, FIG. 1 illustrates an intelligent ball sensor assembly 10 of the present disclosure. The intelligent ball sensor assembly 10 includes a mechanically compliant ball 12 having a recess formed therein.

The ball 12 is mechanically compliant and thus may be formed of soft or flexible material such as foam, silicone, rubber or other suitable material. In some embodiments, the interior of the intelligent ball 12 may comprise a walled rigid central portion of somewhat smaller diameter than the inner diameter of the heat exchanger tube. The walled region (or portion) contains the recess with electronic components and packaging inside of it. This rigid core may in some embodiments be surrounded by a compliant outer structure to allow a degree of flexibility during the ball's transit in the tube and facilitate easy passage. As used herein the term "compliant" refers to a degree of hardness suitable for a particular application. The term "ball" refers to an object that is generally round but may be somewhat oblong, etc. While a spherical or rounded oblong shape is generally preferred, in some embodiments it may be preferable to use a more highly tapered shape, or a shape incorporating ridges, bosses, fins or raised areas to facilitate preferential alignment of the ball inside the tube in one particular orientation or another. A preferred orientation may arise from the desire to sample temperature in one or more regions proximal or distal to the pipe wall.

At least one sensor 14 is combined to the ball 12. The sensor 14 can be positioned inside a recess of the ball 12 or on the surface of ball 12 or positioned elsewhere on the ball 12. The sensor 14 is configured to gather selected information regarding a heat exchanger system 22, as will be discussed below in detail. Signal conditioning control/transmission circuitry 16 is operatively connected to the sensor 14. A power source 18 is operatively connected to the sensor 14 and the signal conditioning control/transmission circuitry 16. The signal conditioning control/transmission circuit 16 can also comprises an RF transmitter. The signal conditioning control/transmission circuit 16 can also comprise a microprocessor with or without memory storage. The microprocessor can cooperate with the sensor 14 and the control/transmission circuitry 16 to determine and calculate the location of the ball in real time. The sensor 14 and the signal conditioning control/transmission circuitry 16 cooperate to gather information about the status, health and efficiency of the heat exchanger system 22.

The sensor 14 may be one or a combination of various sensors. These may include, for example, piezoelectric sensors, temperature sensors, inertial sensors, pressure sensors, chemical sensors, eddy current sensors, magnetic flux leakage sensors, and ultrasonic transducers. The piezoelectric sensors may measure reflected ultrasound and can provide information regarding, for example, cracks, scaling, pinholes, and wall thinning. Or, they may measure acoustic emission and provided information regarding cracks; mechanical failures such as bad pump bearings. The temperature sensors may provide information, for example, regarding bio-fouling or water velocity. The temperature sensor can also be used for measuring the local temperature gradient in a heat exchange tube of the heat exchanger system 22. The inertial sensors may include, for example, angle rate sensor and accelerometers for providing information on, for example, location within heat exchanger and water velocity. A microelectromechanical systems ("MEMS") inertial sensor can deduce reckoning of ball location for determining a precise heat exchanger tube of the heat exchanger system 22 in which the ball enters or exits, thus allowing the characterization of the tube health at the level of individual tubes. The chemical sensors may measure chemical composition and provide information, for example, pH, presence of working fluid or lubricant, or oxidation reduction potential, and/or bio-fouling. The ultrasonic transducer can allow the injection of ultrasonic energy into a wall of a heat exchanger tube of the heat exchanger system, and measurement of reflected power back at the transducer, with a sensor response allowing interpretation of the state and condition of the heat exchanger tube. The ultrasonic transducer can allow the injection of high-frequency ultrasonic energy into fluid in a heat exchanger tube of the heat exchanger system 22, sufficient to create cavitation of the fluid in the heat exchanger tube and achieve ultrasonic cleaning and removal of deposits on the surface of the heat exchanger tube. A magnetic flux leakage sensor can be configured to provide data, the interpretation thereof providing determination of the presence of cracks or pinholes. An eddy current sensor can be configured to provide data, the interpretation thereof being used for determining a level or corrosion or wall thinning.

Some of the sensors 14 may be located within the recess of the mechanically compliant ball 12. Some sensors 14 may be located on or near the surface of the intelligent ball 12, in cases where those sensors 14 need intimate contact with the tube wall or ambient environment.

The signal conditioning control/transmission circuitry 16 takes the signal from these sensors 14 and converts it to a digital value for transmission off the intelligent ball 12. In some cases the sensor 14 output may already be digital. The circuitry 16 may also buffer (store) or otherwise condition or convert the signal. The data is then sent to a transceiver for transmission from the intelligent ball 12 to a central data location, i.e. base station. In some embodiments, this transmission is accomplished by means of a radio (Bluetooth, ZigBee, or some other proprietary or accepted transmission protocol) and in some embodiments it is transmitted by an ultrasonic, near-field or galvanic data link, or other appropriate means. This data would then be received at a central location or at a number of reader nodes.

An intelligent ball sensor assembly 10, through the use of dead reckoning using data from on-board inertial sensors, may sense and calculate position information which can then be used to correlate tube health to individual tubes in the heat exchanger. Furthermore, intelligent balls 12 can communicate with each other and provide ball location determinations using stochastic characterization. Alternately, a method for determining ball location using beacons placed or integrated with the exchanger and received at the intelligent ball 12 could be used. These beacons could be radiofrequency (RF) or ultrasonic beacons, or some other modality from which triangulation could be performed. Thus, as shown in FIG. 1, the signal conditioning control/transmission circuitry 16 is shown with a transmitter 20 for providing transmission to the base station.

In one embodiment, sensors 14 located on the intelligent ball sensor assembly 10 could form a ring around the circumference of the mechanically compliant ball 12, guaranteeing that there would be a sensor in contact with the tube wall, no matter what orientation the ball entered the tube in. Likewise, sensor 14 can be a panoramic lens used to provide a complete field of view of the pipe interior regardless of ball orientation. In another approach the ball 12 is intentionally shape or weighted such that it preferentially orients itself when entering a tube of the heat exchanger. In some cases it may be favorable to design the ball 12 to be somewhat larger than the tube entrance, guaranteeing that the ball was compressed somewhat, bringing sensors 14 into intimate contact with walls of heat exchange tubes 26.

Figure 2:
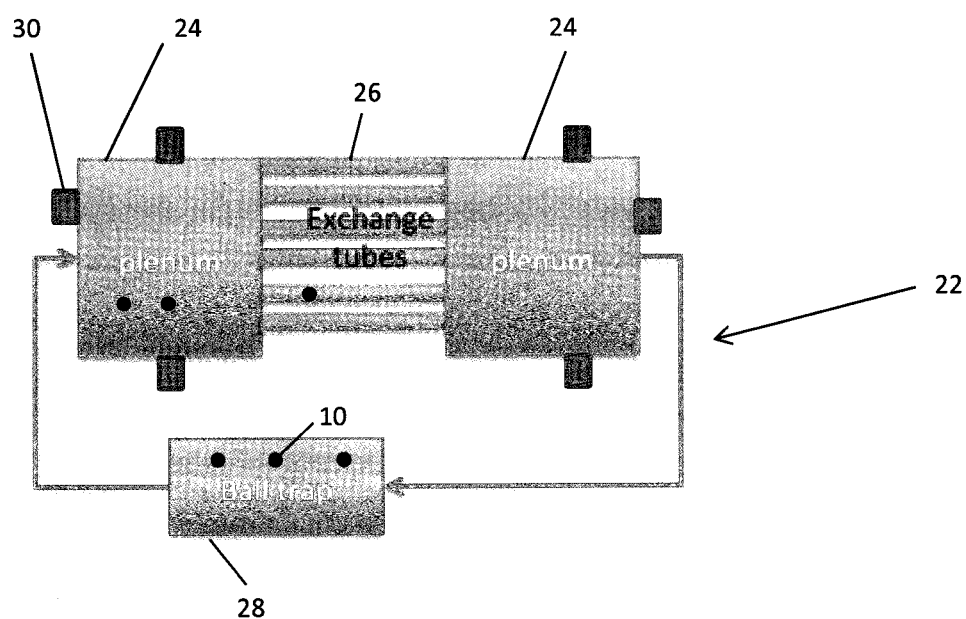
FIG. 2 is a block diagram of a heat exchanger system in accordance with the principles of the present disclosure.

Referring now to FIG. 2, a block diagram of a heat exchanger system 22 in accordance with the principles of the present disclosure is illustrated. The heat exchanger system 22 includes a heat exchanger assembly including a number of plenums, or "water boxes" 24, a number of heat exchange tubes 26 operatively connected to the plenums 24, and a ball trap 28 operatively connected to the plurality of plenums 24.

The heat exchanger system 22 includes a plurality of intelligent ball assemblies, as discussed above relative to FIG. 1.

In one embodiment of a normal operation, each intelligent ball sensor assembly 10 will make a complete circuit of the heat exchanger loop, after which it will be captured in the ball trap 28. In the ball trap 28, sensor data stored by the intelligent ball sensor assembly 10 can be downloaded to a proximal reader (coupled by means of a large data interrogator coil or antenna) for analysis and viewing by the user by means of special software. In some embodiments, the data recorded during transit of the heat exchanger may be transferred from the intelligent ball sensor assemblies to a receiving antenna by means of an RF (radio frequency) link, or by means of an acoustic data communications channel or optical link. The transfer of power from the outside of the ball trap 28 to the balls 12 may be accomplished by an inductive power link operating in either a resonant or non-resonant mode. In some embodiments the ball trap 28 is configured such that when trapped, the balls 12 are forced into a linear configuration (one after the other) in order to allow efficient power coupling from one or more charging coils. Each intelligent ball sensor assembly 10 preferably has a rechargeable power source 18, which may in some embodiments be a battery or supercapacitor. In some embodiments, intelligent ball sensor assemblies 10 may have a means for scavenging power from the environment through thermoelectric or mechano-electrical conversion. After the data download, the intelligent ball sensor assembly 10 is re-initialized and sent back into circulation for another loop. A large number of intelligent ball sensor assemblies 10 completing multiple independent loops insure that data is obtained from every heat exchanger tube 26 over a predicted cycle of timed injections. As described above, the use of positioning information allows the construction of a map of the health of the entire heat exchanger system 22. In some instances, the intelligent ball sensor assemblies 10 locations within the water box related to any specific heat exchange tubes 26 can be assisted with installed beacons (RF) 30 inside the water box that communicates with an internal reference receiver installed inside the intelligent ball sensor assembly. These beacons could be radiofrequency (RF), ultrasonic beacons, infrared plenum beacons or some other modality. Plenum beacon signals from the beacons allow the intelligent ball sensor assembly 10 receiving the plenum beacon signals to record and transmit data regarding certain parameters such as received signal strength or acoustic phase information, from which the reconstruction and interpretation of the data can later be used to determine the heat exchange tube 26 through which the intelligent ball sensor assembly 10 traversed.

The subject inventive concepts have applications to other systems in which tube or pipe health is important. For example, this technology can be used for industrial process monitoring, residential or commercial plumbing, or could be applied to drilling and exploration processes in which a fluid is pumped into a network of fissures and later extracted.

In some embodiments, the intelligent ball sensor assembly 10 can emit or release a signal or tracer that is picked up on the outside of the tube or exchanger for diagnostic purposes (e.g emit IR or x ray radiation or other modality used to image the pipe or screen for holes by detecting the emitted radiation outside the exchanger, or in the case of the tracer, can be detected in the shell side fluid (i.e. outside the tubes) if there is a leak in the tubes.)

In some embodiments the intelligent ball sensor assemblies 10 can communicate to each other in a network topology, via RF or acoustic signaling, to improve location information or enable better communication reliability. For example, an encoded ultrasound signal may be transmitted from each intelligent ball sensor assembly 10 and received by nearby intelligent ball sensor assemblies 10, allowing a determination of distance based on received signal strength. By integrating information about the relative distances and directions between a plurality of intelligent ball sensor assemblies 10 in a network configuration, and between the ball trap and certain intelligent ball sensor assemblies 10 beginning and ending their transit, it may be possible to determine the relative positions of all intelligent ball sensor assemblies 10 in the heat exchanger system 22.

Different transmission means may have certain advantages. For example, ultrasonic communication from ball to receiver or ball-to-ball may provide enhanced power efficiency of data transmission. Data transmission may be in short bursts coincident with intelligent ball sensor assembly recharging.

Cloud enabled software can provide the enabler to track and maintain system maintenance records down to the individual tube level.

The intelligent ball sensor assembly 10 may further include a mercury arc lamp, solid state diode, or other ultraviolet source, which allows the transfer of ultraviolet or other electromagnetic energy into heat exchanger tube fluid of the heat exchanger tube of a heat exchanger system, sufficient to disinfect a surface of the heat exchanger tube.

The smart intelligent ball 12 may contain an electrochemical sensor for chemical or pH detection, as well as an on-board potentiostat for readout, analysis and storage of the electrochemical sensor data, which could be used to determine the pH of circulating water, the presence of electrochemically active substances such as $H2O2$ or Cl, or could be combined with an electrochemical biosensor of interest to measure a wide range of chemicals such as the concentration of refrigerants which would indicate a leak. Also, chemical density detection can be used to correlate direct in reducing levels of water treatment chemicals employed specifically to mitigate fouling inside the heat exchanger tubes.

Although the intelligent ball sensor assemblies 10 have been described relative to their use in a heat exchanger system 22 they may be used in other types of piping systems, such as normal piping systems within a large building, to determine, for example, fluid leaks.

Implemented in piping systems, the sensor may be configured to take UV readings from up to 21 inches from an outer surface of the ball. The mechanically compliant ball is preferably configured to be captured in a portable trapping mechanism after a flow segment run. The sensor may cooperate with the signal conditioning control/transmission circuitry to communicate travel time and location via one of multiple methods including sonic, RF, or stored memory downloaded after a run event.

Other embodiments and configurations may be devised without departing from the spirit of the invention and the scope of the appended claims.

What is claimed is:

1. An intelligent ball sensor assembly for use with a heat exchanger system, comprising:
   a mechanically compliant ball;
   at least one sensor on a surface of or within the mechanically compliant ball configured to gather selected information regarding a heat exchanger system;
   a signal conditioning control/transmission circuitry within the mechanically compliant ball and operatively connected to said at least one sensor; and a power source within the mechanically compliant ball and operatively connected to said at least one sensor and said signal conditioning control/transmission circuitry, wherein said at least one sensor and said signal conditioning control/transmission circuitry cooperate to gather information about a status, health and efficiency of the heat exchanger system.

2. The intelligent ball sensor assembly of claim 1, wherein said at least one sensor comprises a piezoelectric sensor.

3. The intelligent ball sensor assembly of claim 1, and further comprising a transmitter, wherein said at least one sensor comprises a piezoelectric sensor configured to measure reflected ultrasound intensity, which is transmitted by the transmitter to a base station and analyzed upon arrival at a ball trap, in order to determine a state of health and mechanical integrity of a exchanger tube of the heat exchanger system and diagnose cracks, scaling, pinholes, wall thinning.

4. The intelligent ball sensor assembly of claim 1, wherein said at least one sensor comprises a temperature sensor.

5. The intelligent ball sensor assembly of claim 1, wherein said at least one sensor comprises a temperature sensor for measuring a local temperature gradient in a heat exchange tube of the heat exchanger system.

6. The intelligent ball sensor assembly of claim 1, wherein said at least one sensor comprises an inertial sensor.

7. The intelligent ball sensor assembly of claim 1, wherein said at least one sensor comprises a chemical sensor.

8. The intelligent ball sensor assembly of claim 1, wherein said at least one sensor comprises an ultrasonic transducer which allows an injection of ultrasonic energy into a wall of a heat exchanger tube of the heat exchanger system, and measurement of reflected power back at the transducer, with a sensor response allowing interpretation of a state and condition of the heat exchanger tube.

9. The intelligent ball sensor assembly of claim 1, wherein said at least one sensor comprises an ultrasonic transducer which allows an injection of high-frequency ultrasonic energy into fluid in a heat exchanger tube of the heat exchanger system, sufficient to create cavitation of the fluid in the heat exchanger tube and achieve ultrasonic cleaning and removal of deposits on a surface of the heat exchanger tube.

10. The intelligent ball sensor assembly of claim 1, wherein said at least one sensor comprises a magnetic flux leakage sensor configured to provide data, an interpretation thereof providing determination of a presence of cracks or pinholes.

11. The intelligent ball sensor assembly of claim 1, wherein said at least one sensor comprises an eddy current sensor configured to provide data, an interpretation thereof for determining a level or corrosion or wall thinning.

12. The intelligent ball sensor assembly of claim 1, wherein said at least one sensor comprises a MEMS inertial sensor for providing deduced reckoning of ball location for determining a precise heat exchanger tube of the heat exchanger system in which the mechanically compliant ball enters or exits, thus allowing a characterization of the health of the precise heat exchanger tube.

13. The intelligent ball sensor assembly of claim 1, wherein signal conditioning control/transmission circuitry comprises an RF transmitter.

14. The intelligent ball sensor assembly of claim 13, wherein signal conditioning control/transmission circuitry is configured to collect data from the sensor and transmit the data with the RF transmitter to a receiver positioned in a heat exchanger system, and wherein the data is transmitted in short bursts coincident with intelligent ball sensor assembly recharging.

15. The intelligent ball sensor assembly of claim 1, further comprising a mercury arc lamp, solid state diode, or other ultraviolet source, configured to allow a transfer of ultraviolet or other electromagnetic energy into heat exchanger tube fluid of a heat exchanger tube of a heat exchanger system, sufficient to disinfect a surface of the heat exchanger tube.

16. A heat exchanger system, comprising:
a heat exchanger assembly, comprising:
a plurality of plenums;
a plurality of heat exchange tubes operatively connected to said plenums; and,
a ball trap operatively connected to said plurality of plenums; and,
a plurality of intelligent ball sensor assemblies configured to operate within said heat exchanger assembly, wherein each intelligent ball sensor assembly, comprises:
a mechanically compliant ball;
at least one sensor combined to the mechanically compliant ball configured to gather selected information regarding a heat exchanger system;
signal conditioning control/transmission circuitry operatively connected to said at least one sensor; and,
a power source operatively connected to said at least one sensor and said signal conditioning control/transmission circuitry, wherein said at least one sensor and said signal conditioning control/transmission circuitry cooperate to gather information about a status, health and efficiency of the heat exchanger system.

17. The heat exchanger system of claim 16, wherein intelligent ball sensor assembly location is calculated by a microprocessor on the mechanically compliant ball in real time.

18. A heat exchanger system, comprising:
a heat exchanger assembly, comprising:
a plurality of plenums comprising one or more radiofrequency, optical, or infrared plenum beacons;
a plurality of heat exchange tubes operatively connected to said plenums; and,
a ball trap operatively connected to said plurality of plenums; and,
a plurality of intelligent ball sensor assemblies configured to operate within said heat exchanger assembly, wherein each intelligent ball sensor assembly, comprises:
a mechanically compliant ball;
at least one sensor combined to the mechanically compliant ball configured to gather selected information regarding a heat exchanger system;
signal conditioning control/transmission circuitry operatively connected to said at least one sensor; and,
a power source operatively connected to said at least one sensor and said signal conditioning control/transmission circuitry, wherein said at least one sensor and said signal conditioning control/transmission circuitry cooperate to gather information about a status, health and efficiency of the heat exchanger system, wherein plenum beacon signals from the beacons allow the intelligent ball sensor assembly receiving said plenum beacon signals to record and transmit data regarding certain parameters such as received signal strength or acoustic phase information, from which a reconstruction and interpretation of said data can later be used to determine the heat exchange tube through which the intelligent ball assembly traversed.

19. An intelligent ball sensor assembly for use with a piping system, comprising:
   a mechanically compliant ball having a recess formed therein;
   at least one sensor on a surface of or within the recess of the mechanically compliant ball and configured to gather selected information regarding a heat exchanger system;
   a signal conditioning control/transmission circuitry operatively connected to said at least one sensor and positioned in the recess of the ball;
   a power source operatively connected to said at least one sensor and said signal conditioning control/transmission circuitry and positioned in the recess of the ball;
   wherein said at least one sensor and said signal conditioning control/transmission circuitry cooperate to gather information about a status, health and efficiency of the piping system.

20. The intelligent ball sensor assembly of claim 19, wherein said at least one sensor is configured to take UV readings from up to 21 inches from an outer surface of the mechanically compliant ball.

21. The intelligent ball sensor assembly of claim 19, wherein said mechanically compliant ball is configured to be captured in a portable trapping mechanism after a flow segment run.

22. The intelligent ball sensor assembly of claim 19, wherein said at least one sensor cooperates with said signal conditioning control/transmission circuitry to communicate travel time and location via one of multiple methods including sonic, RF, or stored memory downloaded after a run event.

* * * * *